United States Patent
Lee et al.

(10) Patent No.: US 7,780,624 B2
(45) Date of Patent: Aug. 24, 2010

(54) APPARATUS FOR TREATING TUMORS

(75) Inventors: Seung-Hoon Lee, Goyang-si (KR); Yung-Ho Jo, Goyang-si (KR); Heon Yoo, Goyang-si (KR); Sang-Hoon Shin, Goyang-si (KR); Heung-Ki Jeon, Goyang-si (KR)

(73) Assignee: National Cancer Center (KR)

( * ) Notice: Subject to any disclaimer, the term of this patent is extended or adjusted under 35 U.S.C. 154(b) by 292 days.

(21) Appl. No.: 11/789,059

(22) Filed: Apr. 23, 2007

(65) Prior Publication Data

US 2007/0265562 A1 Nov. 15, 2007

(30) Foreign Application Priority Data

May 11, 2006 (KR) .................... 10-2006-0042451

(51) Int. Cl.
*A61M 3/00* (2006.01)
*A61M 1/00* (2006.01)
*A61B 8/14* (2006.01)

(52) U.S. Cl. ............................ 604/43; 604/27; 600/471

(58) Field of Classification Search .................. 604/27, 604/43; 600/471
See application file for complete search history.

(56) References Cited

U.S. PATENT DOCUMENTS

| 4,202,336 A | | 5/1980 | van Gerven | |
|---|---|---|---|---|
| 6,030,379 A | * | 2/2000 | Panescu et al. | ................ 606/34 |
| 2003/0114878 A1 | | 6/2003 | Diederich | |
| 2004/0147987 A1 | * | 7/2004 | Ginsburg et al. | ............ 607/106 |
| 2007/0106204 A1 | * | 5/2007 | Fedenia et al. | ................ 604/28 |

FOREIGN PATENT DOCUMENTS

KR 10-1995-0006145 6/1995

* cited by examiner

*Primary Examiner*—Nicholas D Lucchesi
*Assistant Examiner*—Rebecca E Eisenberg
(74) *Attorney, Agent, or Firm*—Cantor Colburn LLP

(57) ABSTRACT

Disclosed herein is an apparatus for removing fine tumor cells, which remain around a treatment area of patient body, from which a tumor is eliminated, after surgery for removing the tumor has been conducted. The apparatus of the present invention includes a main body, which has a supply tube and a discharge tube that circulate liquid supplied from a storage tank, which is provided outside, and a therapeutic member, which is integrally coupled to an extension pipe that is coupled to the main body and surrounds the supply tube and the discharge tube. A cavity, which communicates with the supply tube and the discharge tube and is supplied with the liquid, is defined in the therapeutic member. The apparatus further includes a temperature sensing unit, which measures a temperature of a treatment area of a patient.

5 Claims, 8 Drawing Sheets

APPARATUS FOR TREATING TUMORS

This application claims priority to Republic Of Korea patent application serial number 10-2006-0042451 filed May, 11, 2006, the disclosure of which is incorporated herein by reference.

BACKGROUND OF THE INVENTION

1. Field of the Invention

The present invention relates generally to apparatus for removing fine tumor cells, which remain around areas of patient bodies from which tumors have been eliminated after surgery for removing the tumors has been conducted and, more particularly, to an apparatus for treating tumors which is inserted into a body cavity formed in a treatment area of a patient body from which a tumor has been removed, after surgery for removing the tumor has been conducted, and eliminates fine tumor cells which remain around the treatment area.

2. Description of the Related Art

Generally, in the case of parts of human bodies such as brains and breasts, after surgery for removing tumors has been conducted, additional treatment is necessary, because tumor cells remaining around treatment areas must be selectively and precisely eliminated without affecting normal cells, unlike other parts of human bodies.

Particularly, in the case of a brain, if normal cells around a tumor are eliminated when the tumor is removed, when the patient recovers, the patient may suffer from side effects, such as severe paralysis, speech disorders and memory failure.

In the case of the breast, unlike the brain, a severe disorder is not induced, but it is necessary to precisely eliminate only tumor cells in order to ensure a normal appearance.

As described above, it is very important to the patient that fine tumor cells, which remain in tissues around a treatment area from which a tumor has been removed, be selectively and precisely eliminated using a separate therapeutic apparatus after the surgery for removing the tumor has been conducted.

Meanwhile, a tumor cell is characterized in that it dies at a temperature of approximately 40° C. to 43° C., unlike a normal cell. A method of removing fine tumor cells, which exist in a patient body, at a relatively high temperature of 40° C. to 43° C. using the above-mentioned characteristics of the tumor cell was proposed and has been used. A treatment method of radiating light and a radiation treatment method using radio frequencies are representative conventional methods of removing fine tumor cells.

However, in the case of the treatment method of radiating light and the radiation treatment method using radio frequencies, treatment is conducted from a position spaced apart from the treatment area of a patient body by a relatively long distance. Therefore, the treatment is also applied to regions other than the treatment area, thus affecting normal cells. As a result, there is a problem in that it is difficult to use these methods in body parts, such as the brain or the breast, in which precise treatment is required.

SUMMARY OF THE INVENTION

Accordingly, an object of the present invention is to provide an apparatus for treating tumors which is harmless to the human body and is able to more precisely and effectively eliminate fine tumor cells, which remain even after surgery for removing a tumor has been conducted.

The present invention provides an apparatus for treating tumors, including: a main body coupled to an outside storage tank and having a supply tube and a discharge tube, through which liquid circulates; a therapeutic member coupled to an extension pipe, which is coupled to the main body and surrounds the supply tube and the discharge tube, with a cavity defined in the therapeutic member and connected to the supply tube and the discharge tube, the cavity being supplied with the liquid; and a temperature sensing unit to measure a temperature of a treatment area of a patient.

Preferably, the therapeutic member may have in a front end thereof a temperature sensor guide hole, through which a part of the temperature sensing unit is inserted and protrudes outside the therapeutic member, and the therapeutic member may be replaceably coupled to the main body such that another therapeutic member having a different diameter is able to be used depending on a size of the treatment area.

The temperature sensing unit may include: a fastening part inserted into the main body and held to the main body by holding means, the fastening part being exposed at a rear end thereof outside the main body to communicate to an outside via signals; a sensor pipe coupled to a front end of the fastening part and inserted into the main body and the therapeutic member; and a temperature sensor provided in a front end of the sensor pipe and protruding from a front end of the therapeutic member to measure the temperature of the treatment area.

Furthermore, the temperature sensor may be provided in a cutting hole formed in the sensor pipe, and a thermal insulator may be provided between the temperature sensor and the cutting hole to prevent the temperature sensor from being affected by heat of the liquid that circulates in the therapeutic member.

The holding means may comprise a plurality of locking grooves formed in an outer surface of the fastening part of the temperature sensing unit at positions spaced apart from each other at regular intervals; and a locking protrusion provided in the main body and locked to one of the locking grooves. Alternatively, the holding means may comprise threads respectively provided on the fastening part of the temperature sensing unit and the main body.

BRIEF DESCRIPTION OF THE DRAWINGS

The above and other objects, features and advantages of the present invention will be more clearly understood from the following detailed description, taken in conjunction with the accompanying drawings, in which.

DESCRIPTION OF THE PREFERRED EMBODIMENTS

Hereinafter, an apparatus for treating tumors according to a preferred embodiment of the present invention will be described in detail with reference to the attached drawings.

Figure 1:
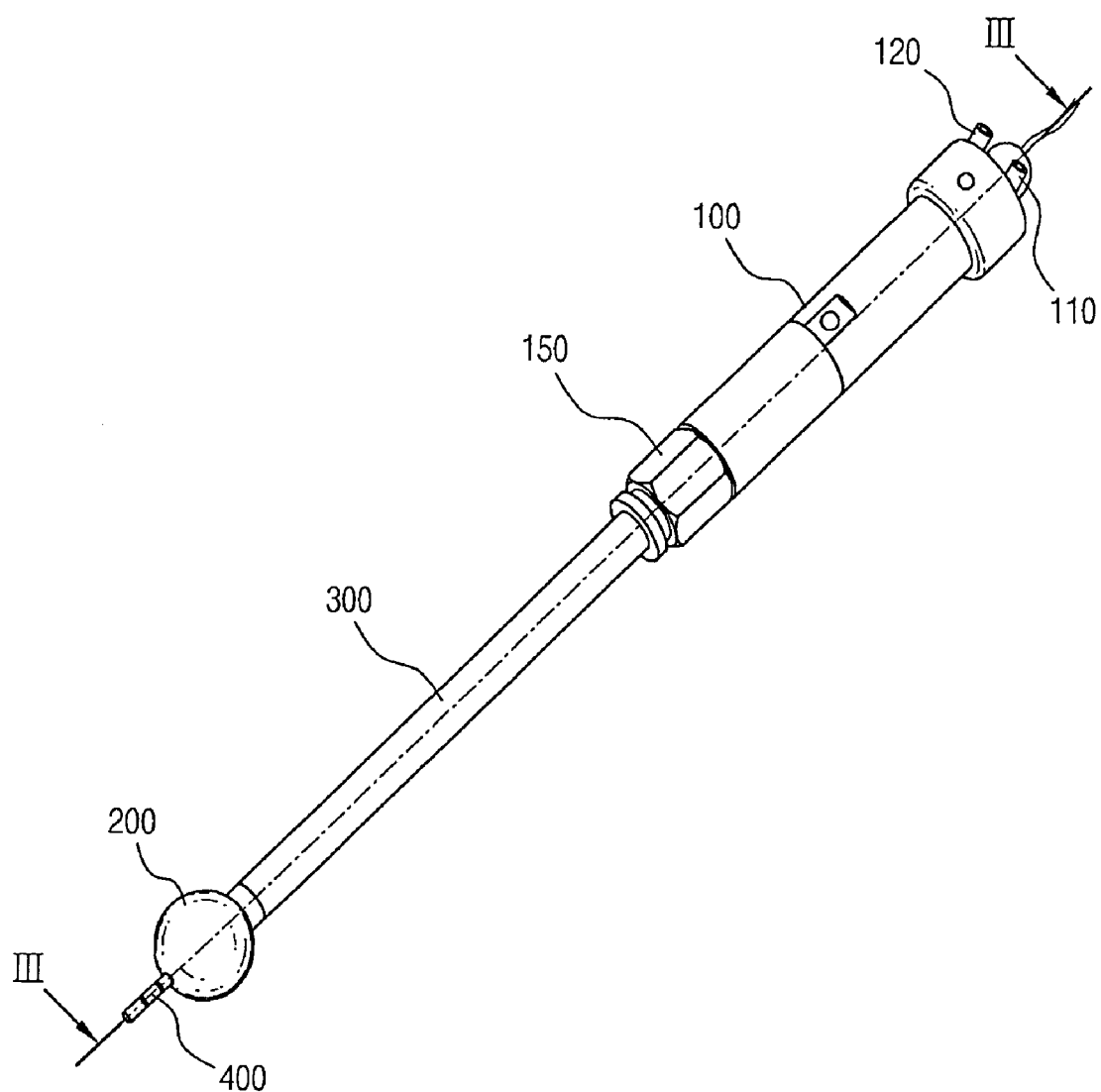
FIG. 1 is a perspective view of an apparatus for treating tumors, according to an embodiment of the present invention.
Figure 2:
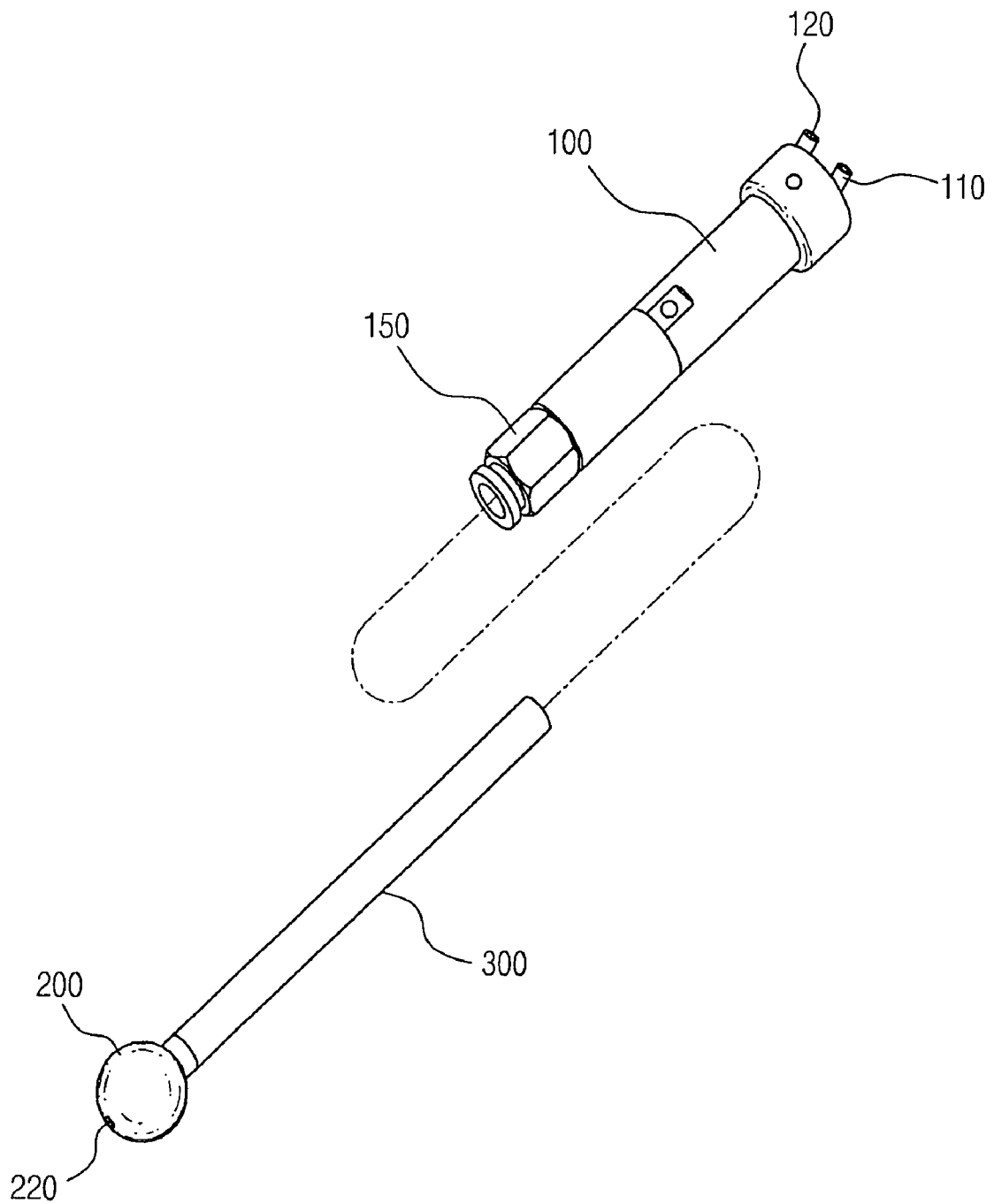
FIG. 2 is an exploded perspective view showing a main body and a therapeutic member of the apparatus of FIG. 1, from which a temperature sensor has been removed.
Figure 3:
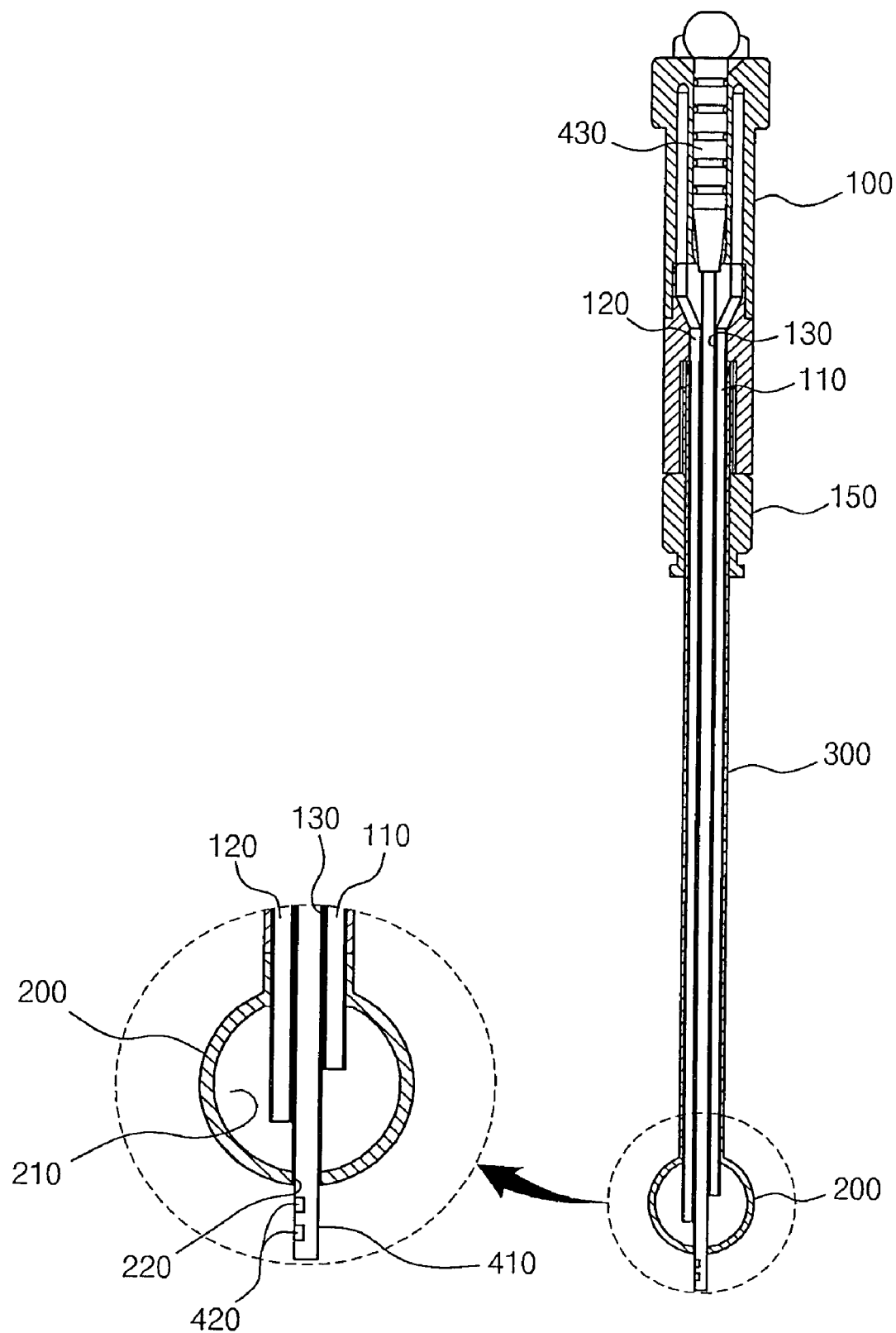
FIG. 3 is a sectional view taken along line III-III of FIG. 1.

As shown in FIGS. 1 through 3, the apparatus of the present invention includes a main body 100, a therapeutic member 200, which is coupled to an extension pipe 300, and a temperature sensor 400.

The main body 100 includes a supply tube 110 and a discharge tube 120, which are constructed such that high-temperature liquid 600 (see, FIG. 7) can be supplied from an outside storage tank 510 (see, FIG. 7) into a cavity 210 defined in the therapeutic member 200 without interruption. The supply tube 110 and the discharge tube 120 are longitudinally provided through the main body 100 and extend to the cavity 210 of the therapeutic member 200. The rear ends of the supply tube 110 and the discharge tube 120 extend outside the rear end of the main body 100 and are coupled to the storage tank 510 through a separate connection means.

Furthermore, a sensor insertion tube 130, into which the temperature sensor 400 is inserted, is provided through the main body 100 along a central axis thereof. Preferably, the main body 100 has a cylindrical shape, but the present invention is not limited to this. In other words, the main body 100 may have a rectangular or hexagonal shape. In addition, an extension pipe coupling part 150 for coupling the therapeutic member 200 is provided on the front end of the main body 100.

The therapeutic member 200 has a sphere shape having the cavity 210 therein, and is coupled at a predetermined position to the extension pipe 300. The extension pipe 300 is coupled to the extension pipe coupling part 150 of the main body 100. Although the extension pipe 300 is illustrated as being press-fitted into the extension pipe coupling part 150 in this embodiment, it may have a structure such that the extension pipe 300 is screwed into the extension pipe coupling part 150.

The therapeutic member 200 has a temperature sensor guide hole 220 in a front end thereof. A temperature sensing unit 420 of the temperature sensor 400 is exposed outside the therapeutic member 200 through the temperature sensor guide hole 220 such that the temperature sensor 420 is inserted into a treatment area, from which a tumor has been removed, to a predetermined depth.

The extension pipe 300 has a cylindrical shape and surrounds the supply tube 110, the discharge tube 120 and the sensor insertion tube 130, which pass through the main body 100 and are coupled to the therapeutic member 200.

Furthermore, the therapeutic member 20Q is manufactured to have various diameters suitable for the sizes of treatment areas of patients, and is replaceably coupled to the main body 100. Therefore, a user prepares several therapeutic members 200 having various sizes, selects a therapeutic member 200 having the size corresponding to the size of the treatment area of a patient, and couples the selected therapeutic member 200 to the extension pipe coupling part 150 of the main body 100.

Generally, a tumor cell dies at a temperature of approximately 40° C. to 43° C., unlike a normal cell.

Hence, the therapeutic member 200 of the apparatus of the present invention is inserted into a body cavity C (see, FIG. 8), which is formed in the body of the patient after surgery for removing a tumor has been conducted, and the therapeutic member 200 is maintained for a predetermined time at the temperature at which the tumor is eliminated. Then, fine tumor cells, which have remained around the treated area of the patient, can be eliminated.

Figure 4:
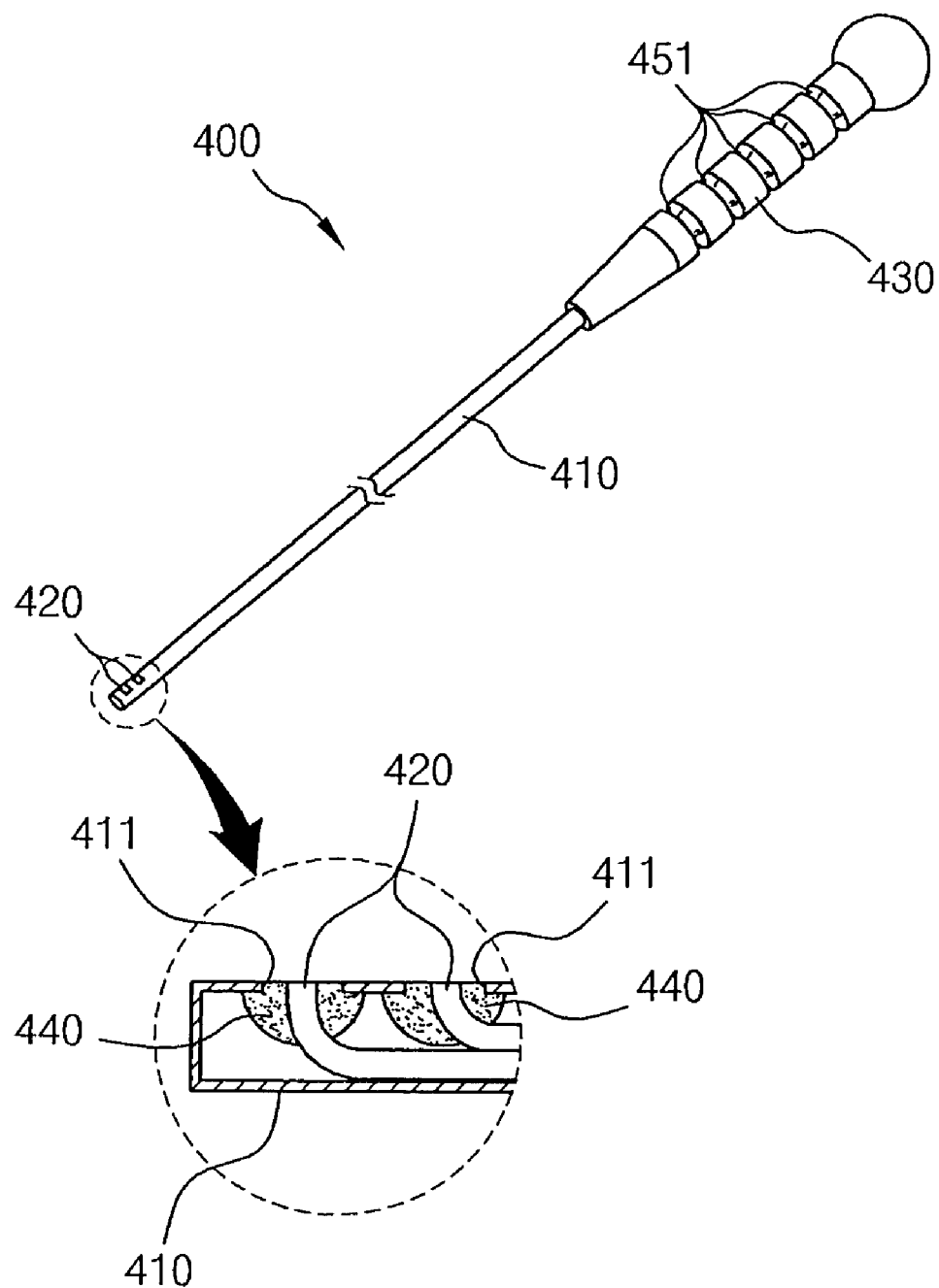
FIG. 4 is a perspective view showing the temperature sensor of the apparatus according to the embodiment of the present invention.
Figure 5:
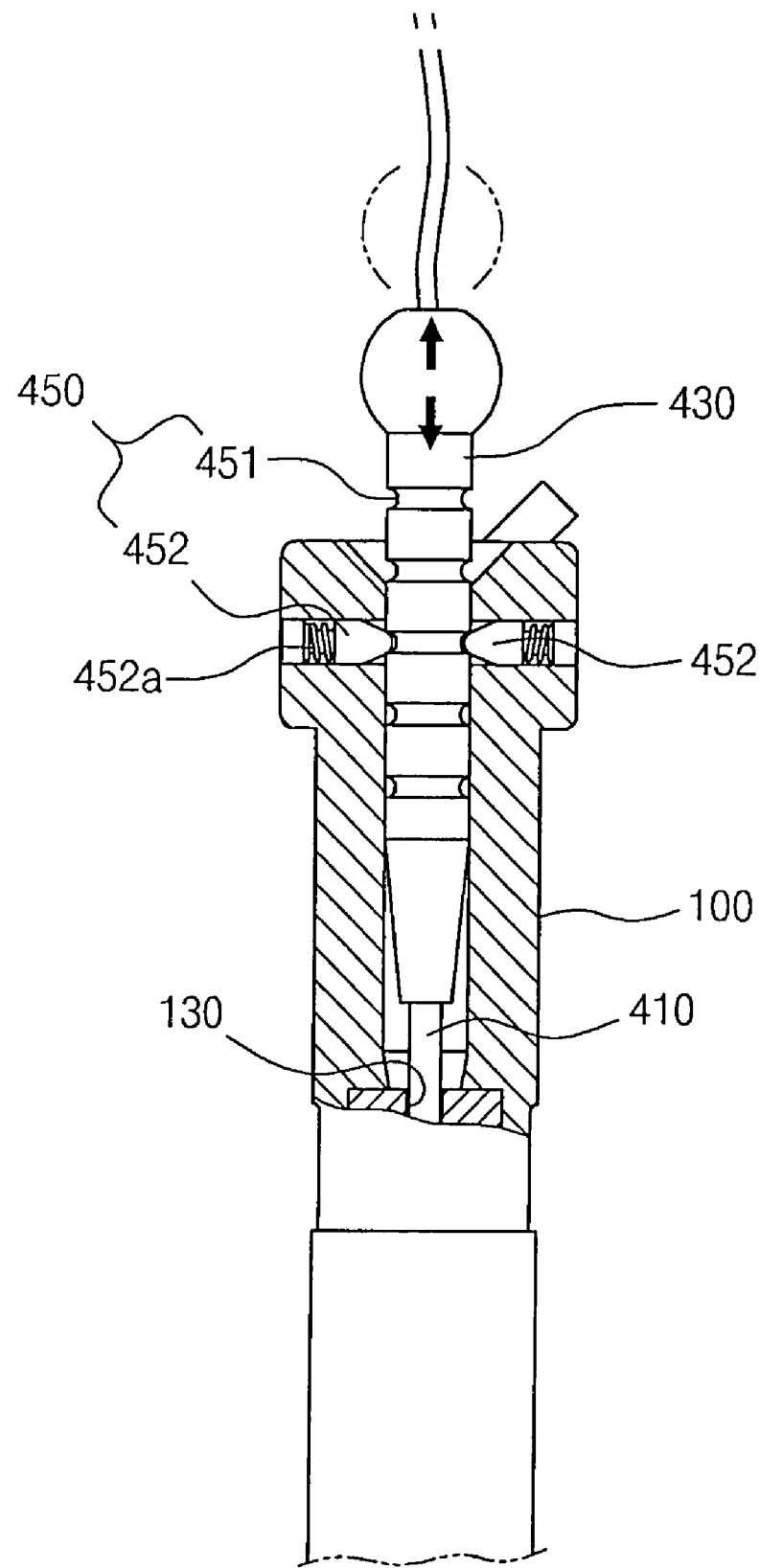
FIG. 5 is a partially enlarged sectional view showing a fastening part of the temperature sensing unit of the apparatus according to the embodiment of the present invention.

As shown in FIGS. 4 and 5, the temperature sensing unit 400 includes a fastening part 430, a sensor pipe 410 and a temperature sensor 420.

The fastening part 430 is held to the main body 100 by a holding means 450, and the rear end of the fastening part 430 is exposed outside the rear end of the main body 100. The holding means 450 includes a locking protrusion 452, which is provided in the main body 100, and locking grooves 451, which are formed in the outer surface of the fastening part 430 at positions spaced apart from each other at regular intervals. The locking protrusion 452 is elastically supported by a spring 452*a*.

The sensor pipe 410 is coupled at a rear end thereof to the front end of the fastening part 430, and has in a front end thereof a cutting hole 411, through which the temperature sensor 420 is exposed. Preferably, the sensor pipe 410 has a circular cross-section.

The temperature sensor 420 serves to detect the temperature of a target region of the treatment area. The temperature sensor 420 is inserted into the sensor pipe 410 and is exposed outside through the cutting hole 411 formed in the front end of the sensor pipe 410. Furthermore, the temperature sensor 420 is constructed such that it communicates with the outside via signals.

The temperature sensor 420 having the above-mentioned construction is a temperature detecting means for monitoring whether heat of high-temperature liquid 600, which circulates in the therapeutic member 200, is evenly transferred to the target region, where the existence of fine tumor cells is expected. The temperature sensing unit 400 is installed in the main body 100 such that the front end thereof protrudes outside through the temperature sensor guide hole 220 formed in the front end of the therapeutic member 200.

Preferably, the temperature sensing unit 400, the front end of which protrudes from the front end of the therapeutic member 200, is constructed such that the distance by which the temperature sensor 420, to be inserted into the treatment area, protrudes from the therapeutic member 200 is adjustable. The reason for this is that the region in which fine tumor cells exist differs depending on the size of the tumor and the conditions of the patient, so that the range within which treatment is required and the time for which treatment is conducted must be changed. That is, the temperature of the target region, in which tumor cells exist, must be precisely measured in order to evenly transfer the heat of the high-temperature liquid 600 to the target region and to efficiently conduct treatment.

To achieve the above-mentioned purpose, the holding means 450 according to the embodiment of the present invention is constructed such that, when the user holds the rear end of the fastening part 430 of the temperature sensing unit 400 and moves it forwards or backwards, the locking protrusion 452 of the main body 100 is locked to one locking groove 451 of the fastening part 430, so that the temperature sensing unit 400 maintains the state of being inserted into and fastened to the main body 100 at a desired position, without being removed from the main body 100. Furthermore, the depth to which the temperature sensing unit 400 is inserted into the main body 100 is adjustable in increments by which the locking grooves 451 are spaced apart from each other.

Figure 6:
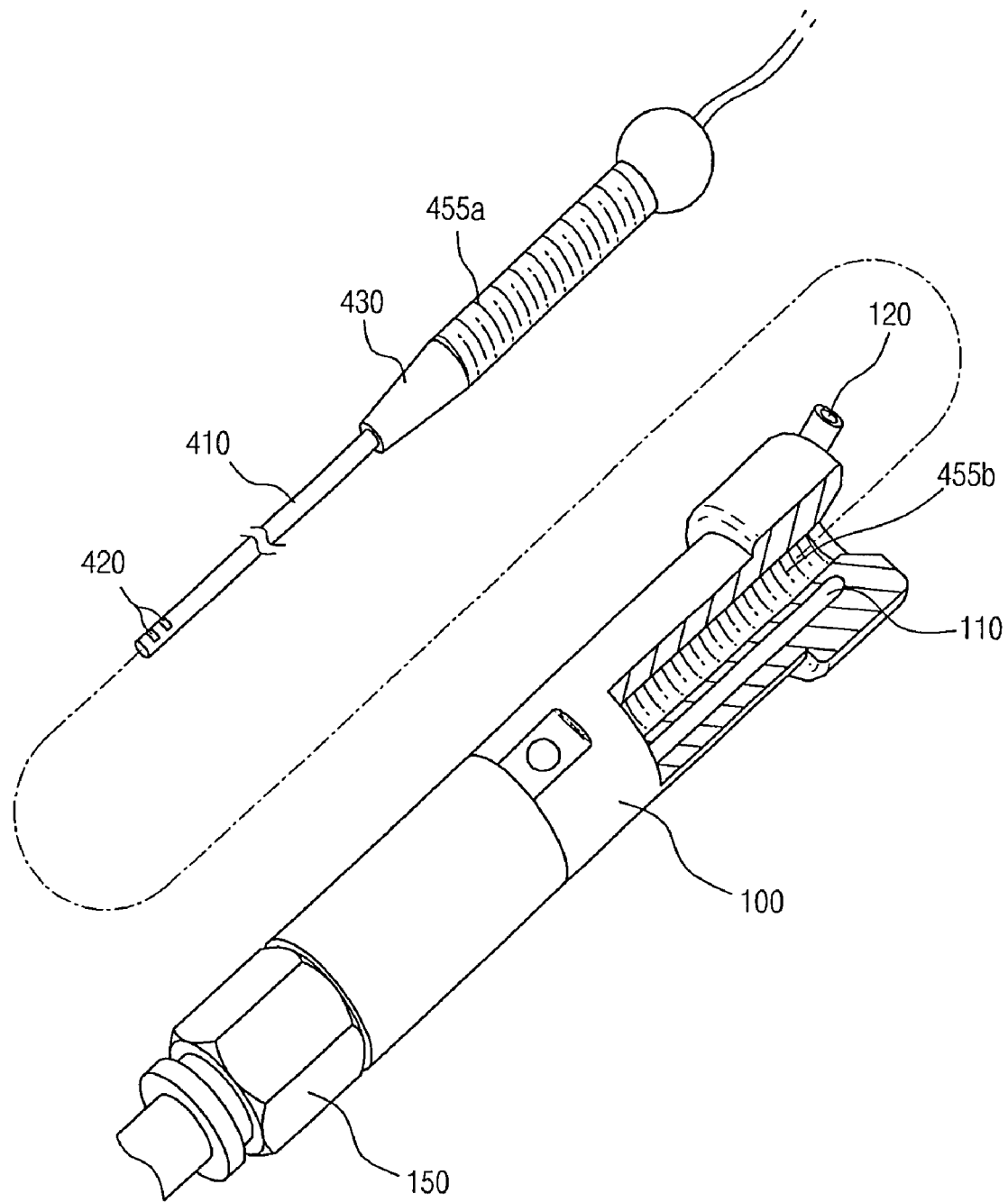
FIG. 6 is a partially broken perspective view showing another embodiment of a holding means of the apparatus according to the present invention.

FIG. 6 shows another embodiment of the holding means 450 of the present invention. The holding means 450 according to this embodiment includes threads 455*a* and 455*b*, which are respectively formed in the fastening part 430 of a temperature sensing unit 400 and a main body 100, unlike the holding means 450 of the prior embodiment, having the locking grooves 451 and the locking protrusion 452.

Therefore, the fastening part 430 of the temperature sensing unit 400 is screwed into the main body 100 through engagement between the threads 455a and 455b of the holding means 450.

As such, when the fastening part 430 is screwed into the main body 100, the depth to which the temperature sensing unit 400 is inserted into the main body 100 can be adjusted by rotating the fastening part 430. In this case, there is an advantage in that the depth to which the temperature sensing unit 400 is inserted into the main body 100 can be variably adjusted within the range given by the threads 455a and 455b without restriction.

Meanwhile, in the present invention, a thermal insulator 440, which prevents the temperature sensor 420 from coming into direct contact with the sensor pipe 410, is provided in the cutting hole 411 of the sensor pipe 410 in order to prevent heat of the high-temperature liquid 600, which circulates in the cavity 210 (see, FIG. 3) of the therapeutic member 200, from being transferred to the temperature sensor 420 through the sensor pipe 410. Therefore, the reliability of the temperature sensor 420 of the temperature sensing unit 400, which measures the temperature of the target region of the treatment area, is increased.

As such, the apparatus of the present invention having the above-mentioned construction can precisely kill tumor cells that remain around the treated area after the surgical operation has been conducted. Therefore, the present invention is useful when removing a tumor from a body part such as the brain, the breasts, etc., where it is necessary to remove the tumor more selectively and precisely compared to other body parts.

The use of the apparatus according to the present invention will be described herein below with reference to FIGS. 7 and 8.

Figure 8:
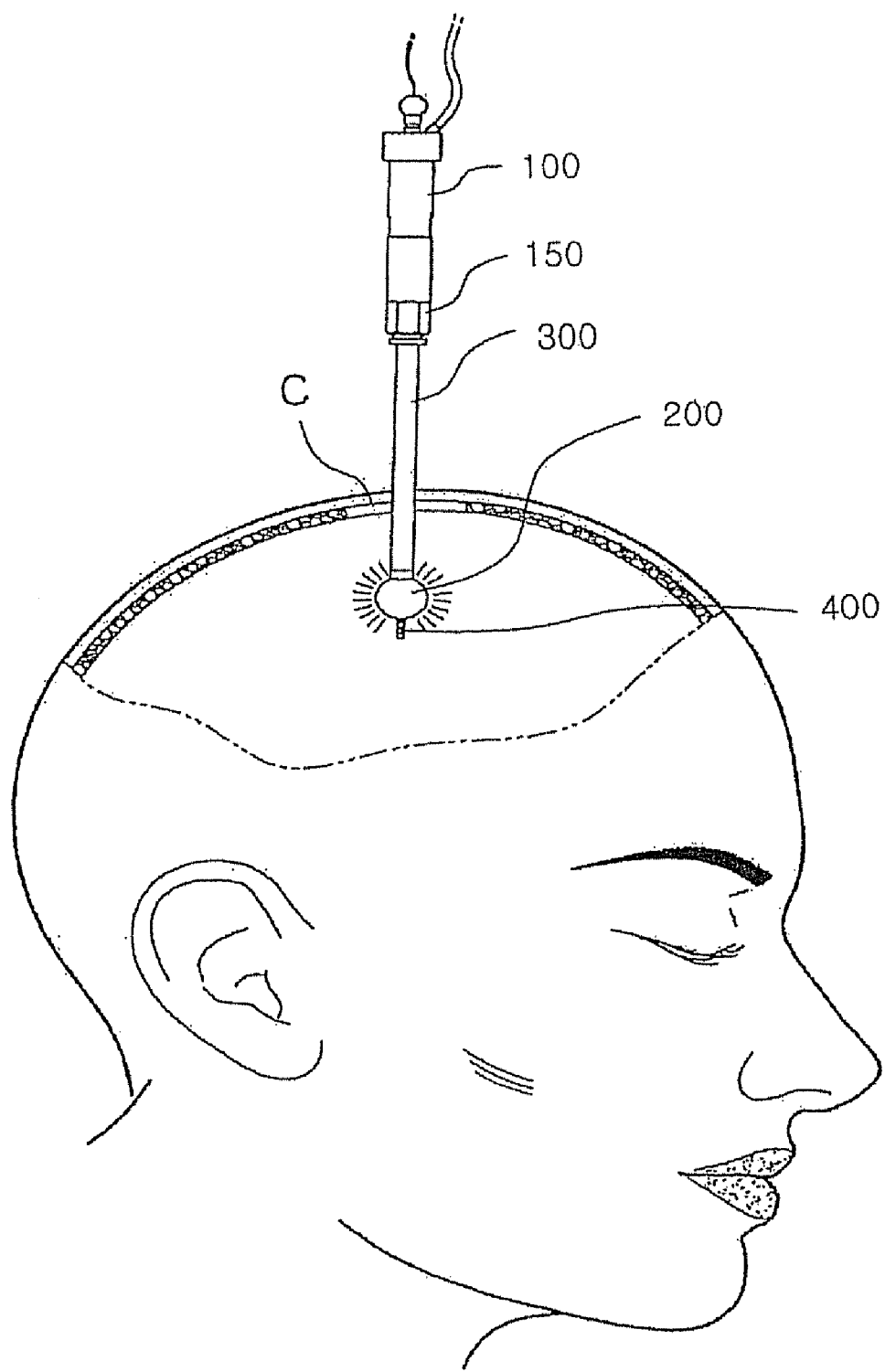

As shown in FIG. 8, after surgery for removing a tumor has been conducted, the user inserts the apparatus, which is assembled with a therapeutic member 200 having a size suitable for a cavity C formed in a body part of a patient by removal of the tumor, into the cavity C. High-temperature liquid 600 is continuously supplied into the therapeutic member 200, so that the treatment area is heated to kill fine tumor cells.

Figure 7:
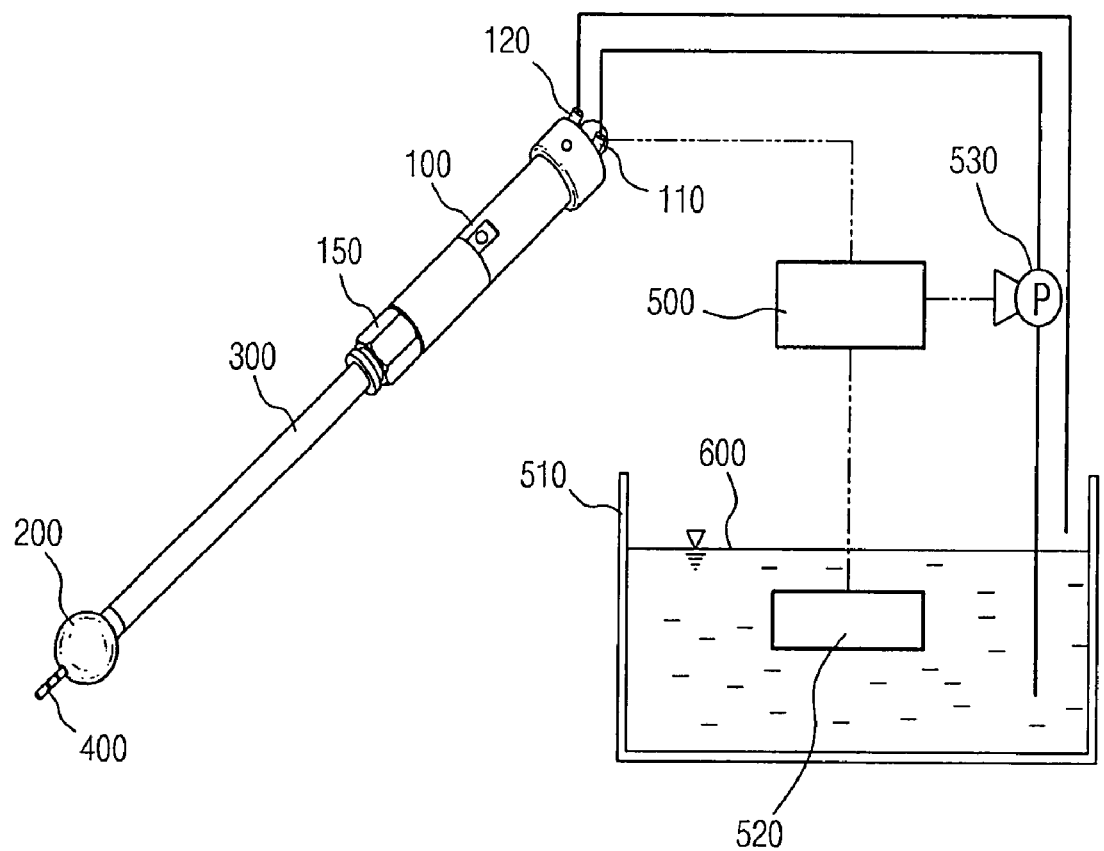
FIGS. 7 and 8 are views showing usage of the apparatus according to the present invention.

Here, as shown in FIG. 7, in the apparatus of the present invention, the supply tube 110 and the discharge tube 120 are coupled to the storage tank 510, which contains the high-temperature liquid 600 therein.

Preferably, distilled water, which is harmless to the patient's body even if it leaks during treatment, is used as the high-temperature liquid 600, which is used for supplying heat to the apparatus, but the high-temperature liquid 600 is not limited to any particular liquid, so long as it is harmless liquid.

High-temperature liquid 600, which is drawn into the supply tube 110 by a supply pump 530, is supplied into the therapeutic member 200 via the main body 100 and the connection pipe 300. Thereafter, the high-temperature liquid 600 is discharged into the storage tank 510 through the discharge tube 120 via the connection pipe 300 and the main body 100. A heater 520 heats high-temperature liquid 600. The control unit 500 is connected to and communicates with the temperature sensor 420 by signals and displays the temperature of the treatment area, which is detected by the temperature sensor 420. Furthermore, the control unit 500 is connected to and communicates with the supply pump 530 and the heater 520, and thus controls the supply pump 530 and the heater 520 such that they are operated appropriately.

As such, the apparatus according to the present invention eliminates tumor cells using the high-temperature liquid 600. Furthermore, in the process of removing the tumor cells, it is very important to precisely control the temperature of the treatment area to increase the effect of treatment.

Meanwhile, the apparatus of the present invention, which is inserted into the treatment area of the patient's body in order to eliminate fine tumor cells which remain around the treatment area, is brought into direct contact with the interior of the patient's body. Thus, the apparatus must be made of metal which is relatively nonreactive with the patient's body. Therefore, it is preferable that the apparatus be made of or be plated with material, such as gold or silver, which is nonreactive with the patient's body.

As described above, unlike the conventional treatment method, in an apparatus for treating tumors according to the present invention, it is easy to maintain an optimal temperature to eliminate tumors from a treatment area, and, because a target region around the treatment area can be intensively treated, there is an advantage in that fine tumor cells can be precisely eliminated. Furthermore, the apparatus of the present invention, which uses liquid, is smaller than the conventional therapeutic apparatus, and manipulation thereof is easier than that of the conventional therapeutic apparatus. In addition, the hyperthermotherapy apparatus of the present invention can precisely eliminate fine tumor cells without affecting a patient's body.

Although the preferred embodiment of the present invention has been disclosed for illustrative purposes, the present invention is not limited to the particular embodiment described above. In other words, those skilled in the art will appreciate that various modifications, additions and substitutions are possible, without departing from the scope and spirit of the present invention as disclosed in the accompanying claims. Furthermore, these modifications, additions and substitutions must be regarded as falling within the bounds of the present invention.

What is claimed is:

1. An apparatus for treating tumors using liquid stored in an outside storage tank, comprising:
    a main body coupled to the storage tank and having a supply tube and a discharge tube, through which the liquid circulates;
    a therapeutic member coupled to an extension pipe, which is coupled to the main body and surrounds the supply tube and the discharge tube, with a cavity defined in the therapeutic member and connected to the supply tube and the discharge tube, the cavity being supplied with the liquid; and
    a temperature sensing unit including a temperature sensor and a sensor pipe containing the temperature sensor, an end portion of the temperature sensing unit protruding from the therapeutic member through a temperature sensor guide hole formed in the therapeutic member to measure a temperature of a treatment area of a patient,
    wherein a distal end of the temperature sensor is exposed to the treatment area through a cutting hole formed in the sensor pipe, and a thermal insulator is provided in the cutting hole to surround the temperature sensor to prevent the temperature sensor from being affected by heat of the liquid that circulates in the therapeutic member.

2. The apparatus as set forth in claim 1, wherein the therapeutic member is replaceably coupled to the main body such that another therapeutic member having a different diameter is able to be used depending on a size of the treatment area.

3. The apparatus as set forth in claim 1, wherein the temperature sensor unit comprises:
    a fastening part inserted into the main body and held to the main body by a holding structure, the fastening part being exposed at a rear end thereof outside the main body to communicate to an outside via signals.

4. The apparatus as set forth in claim 3, wherein the holding structure comprises:

a plurality of locking grooves formed in an outer surface of the fastening part of the temperature sensing unit at positions spaced apart from each other at regular intervals; and a locking protrusion provided in the main body and locked to one of the locking grooves.

5. The apparatus as set forth in claim 3, wherein the holding structure comprises:

threads respectively provided on the fastening part of the temperature sensing unit and the main body.

* * * * *